(12) United States Patent
Potyrailo (10) Patent No.: US 6,383,815 B1
(45) Date of Patent: May 7, 2002

(54) DEVICES AND METHODS FOR MEASUREMENTS OF BARRIER PROPERTIES OF COATING ARRAYS

(75) Inventor: Radislav Alexandrovich Potyrailo, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/681,432

(22) Filed: Apr. 4, 2001

(51) Int. Cl.[7] .............................................. G01N 21/64
(52) U.S. Cl. .............................. 436/2; 436/5; 436/172; 422/82.08; 422/82.11
(58) Field of Search ................................ 436/2, 5, 172; 422/82.08, 82.11

(56) References Cited

U.S. PATENT DOCUMENTS

| | | | |
|---|---|---|---|
| 4,399,099 A | * | 8/1983 | Buckles ........................ 422/58 |
| 4,673,299 A | | 6/1987 | Dakin |
| 5,106,938 A | | 4/1992 | Bookbinder et al. |

(List continued on next page.)

FOREIGN PATENT DOCUMENTS

WO          WO 00/36410          6/2000

OTHER PUBLICATIONS

Rharbi, Y.; Yekta, A.; Winnik, M.A., "A Method for Measuring Oxygen Diffusion and Oxygen Permeation in Polymer Films Based on Fluorescence Quenching", *Anal. Chem.* 1999, 71, 5045–5053.

Lowry, J.H.; Mendlowitz, J.S.; Subramanian, N.S., "Optical Characteristivs of Teflon AF Fluoroplastic Materials", *Opt. Eng.* 1992, 31, 1982–1985.

Buck, W.H.; Resnick, P.R.; "Properties of Amorphous Fluoroploymer Based on 2,2–Bistrifluoromethyl–4,5–Difluoro–1,3–Dioxole", *183$^{rd}$ Meeting of the Electrochemical Society*, 1993.

Mills, A.; Lepre, A., "Controlling the Response Characteristics of Luminescent Porphyrin Plastic Film Sensors for Oxygen", *Anal. Chem.* 1997, 69, 4653–4659.

Lee, S.K.; Okura, I. "Photoluminescent Determination of Oxygen Using MetalloporphyrinPolymer Sensing Systems", *Spectrochim. Acta* 1998, 54A, 91–100.

Amao, Y.; Asai, K.; Miyashita, T.; Okura, I., "Novel Optical Oxygen Pressure Sensing Materials: Platinum Porphyrin–Styrene–Trifluoroethylmethacrylate Copolymer Film", *Chem. Lett.* 1999, 1031–1032.

Prince, Barry J.; Schwabacher, Alan W.; Geissinger, Peter, "A Readout Scheme Providing High Spatial Resolution for Distributed Flourescent Sensors on Optical Fibers", *Anal. Chem.*, 2000, Page Est:8.4 (A–I).

Dakin, J.P., "Distributed Optical Fiber Sensors", *Proc. SPIE–Int. Soc. Opt. Eng.*, 1797, (1992), 76–108.

(List continued on next page.)

*Primary Examiner*—Jeffrey Snay
(74) *Attorney, Agent, or Firm*—Noreen C. Johnson; Christian G. Cabou (57) ABSTRACT

Methods and devices are disclosed for measuring barrier properties of a barrier coating or coating arrays where each barrier coating has a small cross section. To reduce the edge effects in the measurements of barrier properties, measurements are made using a waveguide structure that includes at least one waveguide coated with a chemically sensitive layer and an array of barrier coatings. The coated waveguide is exposed to a material of interest that has the ability to produce an analyzable variation in the chemically sensitive layer, thereby providing the ability to detect an impact of the material of interest on the barrier coatings. In one variation, an initial light wave is propagated within the waveguide structure, a resulting wave associated with the initial wave and each barrier coating is detected, and any impacts on the coatings by the material of interest are correlated to a value of a barrier property for each of the array of barrier coatings.

76 Claims, 3 Drawing Sheets

U.S. PATENT DOCUMENTS

| | | |
|---|---|---|
| 5,233,194 A | 8/1993 | Mauze et al. |
| 5,237,631 A | 8/1993 | Gavish et al. |
| 5,356,668 A | 10/1994 | Paton et al. |
| 5,451,632 A | 9/1995 | Okumura et al. |
| 5,488,086 A | 1/1996 | Umeda et al. |
| 5,519,096 A | 5/1996 | Hara |
| 5,528,040 A | 6/1996 | Lehmann |
| 5,644,017 A | 7/1997 | Drumright et al. |
| 5,674,943 A | 10/1997 | Farah et al. |
| 5,708,957 A | 1/1998 | Chuang et al. |
| 5,717,056 A | 2/1998 | Varadarajan et al. |
| 5,744,794 A | 4/1998 | Michie et al. |
| 5,919,526 A | 7/1999 | Eckberg et al. |
| 5,919,886 A | 7/1999 | Matsuda et al. |
| 5,969,066 A | 10/1999 | Enokida et al. |
| 5,973,068 A | 10/1999 | Yamaya et al. |
| 5,973,126 A | 10/1999 | Ueno et al. |
| 5,981,008 A | 11/1999 | Hofmann |
| 5,981,073 A | 11/1999 | Pickett et al. |
| 5,990,188 A | 11/1999 | Patel et al. |
| 6,010,616 A | 1/2000 | Lewis et al. |
| 6,034,775 A | 3/2000 | McFarland et al. |
| 6,087,181 A | 7/2000 | Cong |
| 6,093,308 A | 7/2000 | Lewis et al. |
| 6,151,123 A | 11/2000 | Nielsen |
| 6,157,449 A | 12/2000 | Hajduk |
| 6,182,499 B1 | 2/2001 | McFarland et al. |

OTHER PUBLICATIONS

Potyrailo, R.A.; Hieftje, G.M., "Optical Time–of–Flight Chemical Detection: Spatially Resolved Analyte Mapping with Extended–Length Continuous Chemically Modified Optical Fibers",*Anal. Chem.*, 1998, 70, 1453–1461.

Potyrailo, R.A.; Hieftje, G.M., "Optical Time–of–Flight Chemical Detection: Absorption–Modulated Fluorescence for Spatially Resolved Analyte Mapping in a Bidirectional Distibuted Fiber–Optic Sensor" *Anal. Chem.* 1998, 70, 3407–3412.

Potyrailo, R.A.; Hieftje, G.M., "Spatially Resolved Analyte Mapping with Time–of–Flight Optical Sensors", *Trends Anal. Chem.*, 1998, 17, 593–604.

Van Dover, R.B.; Schneemeyer, L.F.; Fleming, R.M., "Discovery of a Useful Thin Film Dielectric Using a Composition–Spread Approach", *Nature*, vol. 392, 1998, pp. 162–164.

Hanak, J.J., "The 'Multiple–Sample Concept' in Materials Research: Synthesis, Compositional Analysis and Testing of Entire Multicomponent Systems", *Journal of Materials Science*, 1970, pp. 964–971.

Ward, Michael D.; Buttry, Daniel A., "In Situ Interfacial Mass Detection with Piezoelectric Transducers", *Science*, vol. 249, 1990, pp. 1000–1007.

Hierlemann, A.; Ricco, A.J.; Bodenhöfer, K.; Göpel, W., "Effective Use of Molecular Recognition in Gas Sensing: Results From Acoustic Wave and in Situ FT–IR Measurements", *Anal. Chem.*, 1999, 71, pp. 3022–3035.

Thomas, R.C.; Hierlemann, A.; Staton, A.W.; Hill, M.; Ricco, A.J., "Reflectance Infrared Spectroscopy on Operating Surface Acoustic Wave Chemical Sensors During Exposure to Gas–Phase Analytes", *Anal. Chem.*, 1999,71, pp. 3615–3621.

Furiki, M.; Lyong, S.P., "Hybrid Gas Detector of Squarylium Dye Langmuir–Blodgett Film Deposited on a Quartz Oscillator", *Thin Solid Films*, 1992, pp. 471–473.

Furiki, M.; Lyong, S.P., "Gas Detection by a Multi–Hybrid Sensor with Dye Langmuir–Blodgett Films Deposited on a Quartz Oscillator", *Mol. Cryst. Liq. Cryst.*, 1993, 227, pp. 325–337.

* cited by examiner

DEVICES AND METHODS FOR MEASUREMENTS OF BARRIER PROPERTIES OF COATING ARRAYS

FEDERAL RESEARCH STATEMENT

The U.S. Government may have certain rights in this invention pursuant to contract number 70NANB9H3038 awarded by the National Institutes of Standards and Technology (NIST).

BACKGROUND OF INVENTION

The invention relates to devices and methods for determining barrier properties of coatings, and more particularly, to combinatorial barrier property screening devices and methods.

Coatings having barrier properties are used for many packaging and protective applications. The coatings, as barriers, typically separate a system, such as an electronic component, a part of an engineering structure or an article of food, from an environment. As such, the barrier properties of the coating define the permeability or resistance of the particular coating to a given material of interest. For example, typical barrier properties include the resistance of a coating to oxygen or to moisture.

In an effort to discover new and improved coating formulations, the analysis of new coatings is limited by the large sample sizes and long exposure time periods typically required for screening each new coating formulation. The large sample size and long exposure times to one or more materials of interest to test a coating formulation are generally required in order to detect the transport of the material of interest through the coating. Because the barrier properties of a coating may be high, only small amounts of the material of interest may penetrate the coating and/or it may take a long time for such penetration.

For example, the transport of oxygen through a coating is typically measured by exposing one side of the coating to oxygen, while nitrogen gas sweeps the other side of the coating to an oxygen detector. The detector measures the rate that oxygen comes through the coating. In order for the detector to receive a measurable amount of oxygen, a large sample size is utilized. Same approach is utilized for measurements of moisture permeability of coatings, where a water vapor detector used instead. Besides the disadvantage of requiring a large surface area, another problem with this technique is the difficulty of mapping oxygen or/and water vapor transport of different spatial regions of the single coating or performing evaluation of multiple coatings with the same detection system simultaneously.

Another disadvantage of typical barrier coating measurement techniques is that the edges of the coating typically mischaracterize the measurement results if the cross section of the analyzed barrier coating is small. This "edge effect" provides another factor to account for in measuring and analyzing new coating formulations, thereby reducing the efficiency of the process.

Thus, there remains an unmet need to provide devices and methods for efficiently measuring the barrier properties of a coating or combination of coatings. There remains a further need to provide devices and methods such that measurement errors associated with coating edge effects are reduced or eliminated.

SUMMARY OF INVENTION

The present invention discloses methods and devices for measuring barrier properties of coating arrays.

In one embodiment, a device for measurement of barrier properties of barrier coatings includes a waveguide having an external surface with a chemically sensitive layer disposed about the external surface of the waveguide, where the chemically sensitive layer is responsive to a material of interest. A predefined number of barrier coatings are deposited onto the chemically sensitive layer, and each of the barrier coatings has a corresponding barrier property with respect to the material of interest. A light source is operable to propagate a wave within the waveguide, and a detector is operable to measure impacts associated with the propagated wave and associated with the respective barrier property of each of the plurality of barrier coatings. A correlator correlates the measured impact with a value of the barrier property for each of the plurality of barrier coatings.

In another embodiment, a method for measuring barrier properties of coating arrays includes applying a chemically sensitive layer to an exterior surface of a waveguide, where the chemically sensitive layer has at least one characteristic that changes in response to exposure to a material of interest. Also, the method includes applying an array of barrier coatings to the chemically sensitive layer, where each coating of the array of barrier coatings has a barrier property with respect to the material of interest. A wave is transmitted through the waveguide and the waveguide with the applied array of barrier coatings is exposed to the material of interest. The impact associated with the propagated wave is detected and correlated with a value of a barrier property for each of the array of barrier coatings.

Additional advantages and novel features of the invention will be set forth in part in the description that follows, and in part will become more apparent to those skilled in the art upon examination of the following or upon learning by practice of the invention.

DETAILED DESCRIPTION

One embodiment of the present invention includes a system for evaluation of barrier properties of coatings applied to the surface of a waveguide and detected using optical time-of-flight (OTOF) information for a pulsed light or other wave propagated via the waveguide. In an embodiment of the present invention, one or more barrier coatings are applied onto the surface of a dielectric waveguide, which may be of any geometry. In one embodiment, the waveguide is preferably a cylindrical geometry. In these embodiments, edge effects are eliminated, provided that a coating is applied over the entire cross section of a waveguide, and provided that the length of the coating is much longer than the coating thickness.

References will now be made in detail to embodiments of the present invention, examples of which are illustrated in the accompanying drawings.

Figure 1:
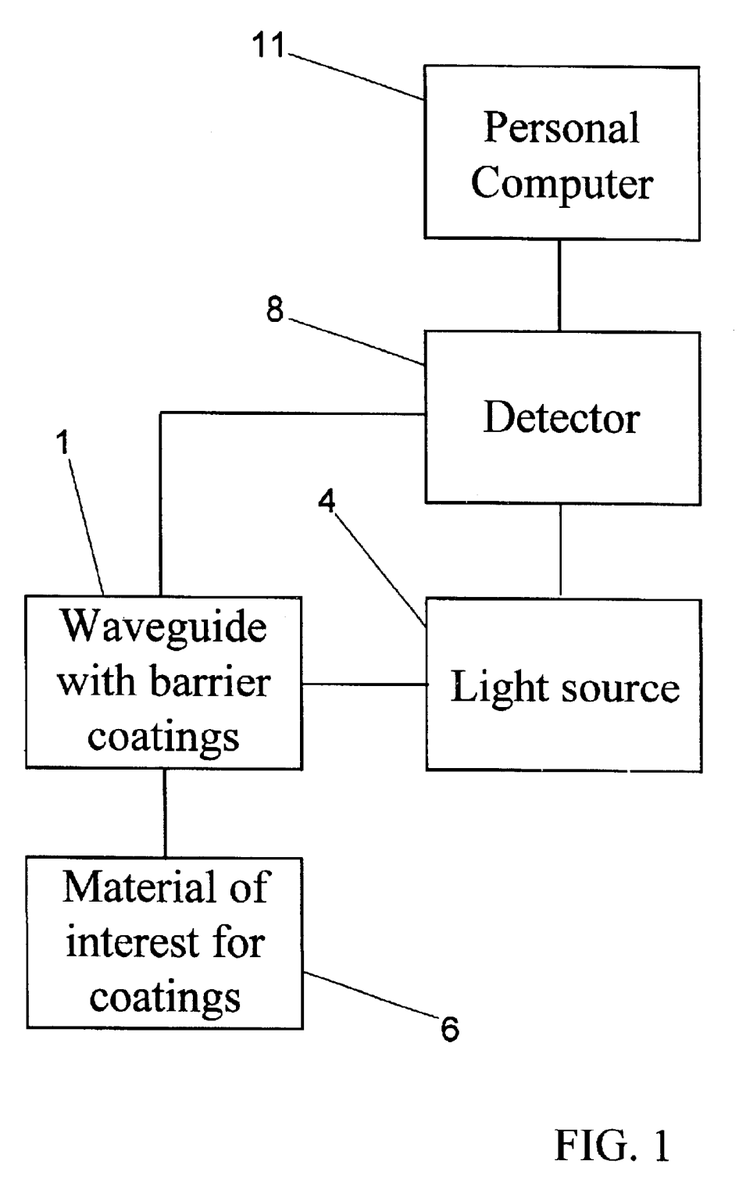
FIG. 1 presents a functional diagram of the various components of a waveguide device in accordance with an embodiment of the present invention.

FIG. 1 presents a functional diagram of the various components of an embodiment of the present invention for analyses using waveguides with barrier coatings applied. As shown in FIG. 1, the waveguide having a plurality of barrier coatings applied 1 is coupled to a light source 4 that transmits light to the waveguide 1. A detector 8 detects the propagated light within the waveguide with the barrier coating applied 1. And, in one embodiment, a separate display device 11 such as a personal computer, digitizing oscilloscope or another type of display is coupled to the detector 8 for displaying the detected light. With, for example, a chemical, solvent, or other material of interest 6 exposed to the barrier coated waveguide 1, an impact on or variation in the barrier coating that affects the propagated light is detectable by the detector 8. Such detection is then used to determine the barrier properties of the coatings with improved precision. In an alternate embodiment, a similar set-up may be utilized but with one of the plurality of barrier coatings applied to a corresponding one of a plurality of waveguides each connected to the light source, such that a single coating is deposited on each waveguide.

The principle of operation is as follows. When a pulse of light at probe wavelength $\lambda 1$ is launched into a waveguide, analytical information can be derived from the portion of light which is returned to the launch end of the waveguide. The analytical signal might be the Rayleigh backscatter at wavelength $\lambda 1$ or luminescence emission at a different wavelength $\lambda 2$. The Rayleigh and luminescence signals are modulated by variations in concentration of the material of interest at the waveguide—sensing layer interface.

The Rayleigh scattering usually originates from microscopic inhomogeneities in the waveguide material. These inhomogeneities cause spatial fluctuations in the refractive index of the waveguide and generate reflections of light guided in the waveguide. A portion of the scattered light is recaptured by the waveguide numerical aperture in the reverse direction.

In a device for measurements of barrier properties of coating arrays made from a multimode dielectric waveguide and coated with a chemically sensitive layer, detection of a material of interest transported through the barrier coating can be based on Rayleigh backscatter. It can utilize either variations in the refractive index or absorption coefficient of the chemically sensitive layer on the waveguide. These variations modulate the intensity of the backscatter signal because of losses in the evanescent field. If the chemically sensitive layer on the waveguide is doped with a fluorophore, the evanescent wave will excite the fluorophore at the waveguide/sensing layer interface. Half of the luminescence emission recaptured by the waveguide numerical aperture will be guided toward the launch end of the waveguide. Alternatively, the wave resulting from the interaction of the propagated wave and the coating/sensor combination may be detected and its characteristics may be measured at the end of the waveguide opposite the launching end.

To obtain information about the location of a material of interest, that is, where a change in the back propagated radiation occurs (as measured from the launch end of the waveguide), the level of the returned signal is monitored as a function of the time delay between the launched and returned light pulse. See, e.g., R. A. Potyrailo and G. M. Hieftje, "Optical Time-of-Flight Chemical Detection: Spatially Resolved Analyte Mapping with Extended-Length Continuous Chemically Modified Optical Fibers," *Anal. Chem.* 70, 1453–1461 (1998) The relation between the location/of interest along the waveguide and the time t required for the light pulse to propagate forward and backward to this location is given by:

$$t = l(n_f + n_b)/c, \quad (1)$$

where c is the velocity of light in vacuum, and nf and nb are the refractive indices of the waveguide at the wavelengths of the forward (excitation wavelength) and backward (analytical wavelength) propagated pulses.

To increase the signal level and to improve the signal-to-noise ratio (S/N), repetitive light pulses should be used. However, only a single pulse should propagate in the waveguide at a given time to avoid signal overlap. Thus, the maximum pulse repetition rate Fmax is limited by the length L of the waveguide and is given by $$F_{max} = c/(n_f + n_b)L. \quad (2)$$

The returned signal in an OTOF measurement system was first formulated for Rayleigh backscatter and then for Raman backscatter. If the relationship is generalized also for luminescence detection, the backpropagated impulse response from a distance/along the waveguide excited by a $\delta$-pulse is given by $$P(l) = rP_o S(l) \exp\{-\int[\alpha_f(z) + \alpha_b(z)]dz\} \quad (3)$$

where Po is the excitation power in the input pulse coupled into the waveguide, r is the ratio of the transmitted to the reflected optical power in the beamsplitter, S is a constant that depends on the local numerical aperture (NA) of the waveguide, the luminescence quantum yield of the immobilized fluorophore (in a luminescence-based sensor), or on the Rayleigh and Raman scattering parameters of the waveguide (in a scattering-based device ), and $\alpha$ f(z) and $\alpha$ b(z) are the attenuation coefficients of the forward and backward traveling pulses, respectively. In luminescence-based devices, both $\alpha$ f and $\alpha$ b have two components, one each for the excitation and emission wavelengths.

The response of an OTOF device based on attenuation detection is a convolution of the ideal impulse response described by eq 3 and the temporal profile Rex(t) of the excitation pulse width $\tau$ ex. By using a transformation of variables I→t given by eq 1, the response Patt(t) of an attenuation-based OTOF device can be expressed as $$P_{att}(t) = P(t) \otimes R_{ex}(t), \quad (4)$$

where $\otimes$ denotes convolution. Similarly, the response Pfl(t) of a luminescence-based OTOF device is given by $$P_{fl}(t) = P(t) \otimes R_{ex}(t) \otimes R_{em}(t) \quad (5)$$

where Rem(t) is the impulse response of the immobilized fluorophore (i.e. an exponential decay having a time constant equal to the luminescence lifetime $\tau$ em of the fluorophore).

In a device based on a statically quenched immobilized fluorophore, $\tau$ em is constant. The output signal of such a device is a function of the attenuation coefficient of the immobilized fluorophore. This functional dependence is similar to that of an attenuation (absorption-based) device.

A device based on dynamic luminescence quenching of an immobilized fluorophore does not exhibit a change in attenuation coefficient upon exposure to a quencher. Rather, the luminescence lifetime $\tau$ em and emission intensity I are a function of the quencher concentration [Q] as described by the Stern-Volmer equation:

$$I_o/I = \tau_{o_{em}}/\tau_{em} = 1 + K_{sv}[Q] \quad (6)$$

where Io and $\tau$ oem are the emission intensity and luminescence lifetime of the fluorophore in the absence of the quencher and Ksv is the Stern-Volmer quenching constant.

Figure 2:
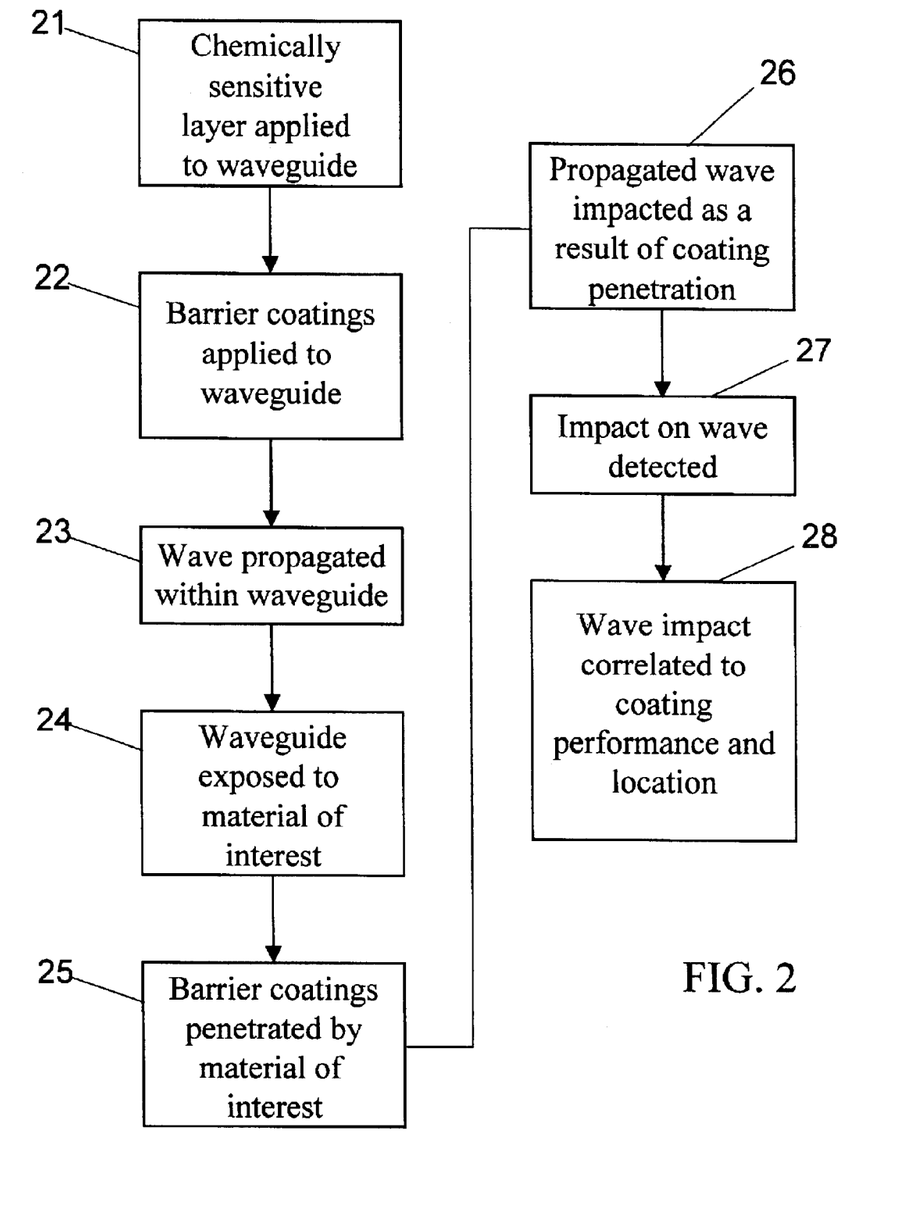
FIG. 2 is a flow diagram of a method for measuring properties of coating arrays in accordance with an embodiment of the present invention.

FIG. 2 is a flow diagram of a method for measuring barrier properties of coating arrays in accordance with an embodiment of the present invention. As shown in FIG. in an embodiment of the present invention, a sensor layer such as a chemically sensitive layer is initially applied to a waveguide (Block 21). The waveguide includes, for example, an optical fiber made of quartz, a polymer, or other types of dielectric materials commonly used to manufacture optical fibers. Such waveguides are available as optical fibers of different diameters of fiber core, typically ranging from about 2 micron to about 2000 micron. The chemically sensitive layer is a material that is responsive to exposure to a material of interest for which a coating is designed to provide a barrier, and for which the response is measurable by a detecting device. After coating with the chemically sensitive layer, one or more barrier coatings are then applied to the waveguide (Block 22). Materials for barrier coatings include, but are not limited to, organic and inorganic materials, blends, composites, and their combinations, oxides, nitrides and oxinitrides of silicon, aluminum, zinc, boron and other metals, ceramics, polyvinyl alcohol, ethylene vinyl alcohol copolymers, polyvinyl dichloride, different types of nylon, cellophane, polyethylene terephtalate, PVC, PCTFE, polypropylene, combinations thereof as well as other similar materials typically used to provide a barrier to transport of a given material of interest. Materials for barrier coatings are also those being developed using combinatorial chemistry and high throughput screening approaches. Further, the predetermined number of barrier coatings may include one coating, or a plurality of different barrier coatings. A barrier coating has a set of parameters that may be varied, the parameters including composition, thickness, and coating preparation conditions such as environment, method, curing, and other parameters. Each barrier coating on the wave guide may have a small cross-section and length along the axis of the waveguide. In general, the cross-section or thickness of each coating may be in the range of about 0.1 nanometers to about 100 micrometers, particularly in the range of about 1 nanometer to about 10 micrometers, and more particularly in the range of about 10 nanometers to about 5 micrometers. The length along the waveguide of each barrier coating may be in the range of about 1 millimeter to about 10 meters, particularly in the range of about 5 millimeters to about 1 meter, and more particularly in the range of about 1 centimeter to about 50 centimeters. The edge effects which would normally provide inaccurate results are eliminated by measuring the detected light within the waveguide.

Generally, an analysis is made of the barrier properties of each coating such as susceptibility to penetration/transport or permeability to a material of interest 6 to which the coatings 1 are exposed. After initially applying the barrier coatings to the waveguide (Block 22), a wave, such as a generated light pulse, is propagated within the waveguide and the impact on the propagated wave is detected (Block 23). For example, the wave has associated initial characteristics, such as frequency, amplitude and phase, as it is forward-propagated within the waveguide. As the wave interacts with a given coating/sensor combination, the initial characteristics of the wave may be changed and this change can be detected by measuring the associated back-propagated wave. Alternatively, as the wave interacts with a given coating/sensor combination, the wave may cause a response of another wave to be generated from the sensor layer, and this new back-propagated wave is measured. The difference between the initial characteristics of the forward-propagated wave and the characteristics of the back-propagated wave is referred to as the impact on the wave. The initial measurement establishes a baseline measurement and verifies the initial state of each coating. The wave may be measured by, for example, a photodetector coupled to an oscilliscope, or any other similar wave measurement device.

Then, another wave is propagated in the waveguide while the waveguide is exposed to the material of interest 6 (Block 24). For example, suitable materials of interest 6 include oxygen gas, liquid water, moisture or water vapor, organic and inorganic vapors, combinations thereof, and other similar materials in any phase, but preferably as a liquid or gas. One or more barrier coatings then becomes affected, such as through penetration by or transport of the material of interest through the coating (Block 25).

As a result of the interaction between the material of interest 6 (FIG. 1) with the chemically sensitive layer after transport of the material of interest through one or more barrier coatings 1, the propagated wave within the waveguide is impacted or the propagated wave causes a measurable impact, i.e. fluorescence (Block 26). The impact on the wave is defined as a measurable change in the wave, such as a variation in amplitude, frequency, polarization state, phase and temporal properties of the wave. The impact caused in the wave corresponds to and is correlated with a measurable change of the characteristics of the respective barrier coating. For example, the propagated wave may be affected by luminescence in the chemically sensitive layer caused by transport of the material of interest through the coating. The impact is determined relative to the initial state of the coating by comparing the measured result of the later-propagated with the measured result of the initially-propagated wave. The impacts of the later-propagated wave are detected (Block 27) and then correlated to a coating location (Block 28), and optionally displayed on a display device (see FIG. 1), such as a monitor coupled to a processor of a computer or on a display associated with the measurement device. Further, the impact is correlated to an amount of a barrier characteristic in such a way that the relative performance of each of the plurality of barrier coatings may be analyzed and compared to determine relative performance of each coating with respect to the material of interest.

Coatings 1 (FIG. 1) may be analyzed in this manner to measure a number of barrier properties. Suitable barrier properties include permeability and other similar barrier properties. Gas permeation properties of coatings are typically characterized by: either the steady state gas permeation rate, also called the transmission rate, defined as the volume of gas at standard temperature and pressure passing through a unit area of the coating per second divided by the pressure difference across the coating; or the steady state gas permeability defined as the permeation rate times the thickness of the coating. In the case of permeants (such as oxygen) that do not strongly interact with the coating, the permeability is a fundamental property of the coating, independent of coating thickness. In this case it is called intrinsic permeability.

The composition of the chemically sensitive layer varies depending on the particular barrier property and material of interest being analyzed. Characteristics of the chemically sensitive layer, such as absorption spectrum, refractive index, luminescence intensity, luminescence lifetime, luminescence spectrum, etc. may change upon exposure to the material of interest. The chemically sensitive layer is a film deposited onto the waveguide and responsive to a material of interest. The chemically sensitive layer can consist of an analyte-responsive material (such as inorganic or organic material) and optionally a chemical reagent. Upon exposure to the material of interest, the chemically sensitive layer is affected by the material of interest.

The optical property of the layer upon material sorption can be changed by the optical property of the material. For example, if a pure material absorbs radiation at a certain wavelength, then the chemically sensitive layer, after exposure to this material, will absorb radiation at the same wavelength proportionally to the material concentration in contact to the layer. If a pure material emits radiation at a certain wavelength, then the chemically sensitive layer after exposure to this material will emit radiation at the same wavelength proportionally to the material concentration in contact to the layer. Other optical parameters that can be altered upon contact with the analyte material are refractive index of the layer and the amount of light scattered or diffused by the layer. If the material does not possess the readily measurable optical property at a given concentration, the chemical reagent is selected to be incorporated into the layer. The chemical reagent changes its optical property (typically UV-visible-IR absorption and/or luminescence spectra).

A sensor layer comprises at least one class of chemically sensitive reagents. One class of reagents includes porphyrins. Examples of the porphyrins include but are not limited to tetraphenylporphyrin, metal porphyrins, such as platinum (II) octaethylporphyrin (Pt-OEP) and palladium(II) octaethylporphyrin (Pd-OEP), and others as described in P. Hartmann, W. Trettnak, "Effects of polymer matrices on calibration functions of luminescent oxygen sensors based on porphyrin ketone complexes," Anal. Chem. 1996, 68, 2615–2620; A. Mills, A. Lepre, "Controlling the response characteristics of luminescent porphyrin plastic film sensors for oxygen," Anal. Chem. 1997, 69, 4653–4659; Potyrailo, R. A.; Hieftje, G. M., Oxygen detection by fluorescence quenching of tetraphenylporphyrin immobilized in the original cladding of an optical fiber, Anal. Chim. Acta 1998, 370, 1–8.

Another class of reagents includes polycyclic aromatic hydrocarbons. Examples and applications of this class of fluorophores are described by: I. B. Berlman, Handbook of luminescence spectra of aromatic molecules, Academic Press, New York, N.Y., 1971; O. S. Wolfbeis, Fiber Optic Chemical Sensors and Biosensors; O. S. Wolfbeis, Ed.; CRC Press: Boca Raton, Fla., 1991; Vol. 2; pp 19–53; Hobbs, S. E.; Potyrailo, R. A.; Hieftje, G. M., Scintillator light source for chemical sensing in the near-ultraviolet, Anal. Chem. 1997, 69, 3375–3379. Preferred fluorophores of this class include pyrene, pyrenebutyric acid, fluoranthene, decacyclene, diphenylanthracene, and benzo(g,h,l)perylene.

Another class of reagents includes a variety of long-wave absorbing dyes such as perylene dibutyrate, and heterocycles including fluorescent yellow, trypaflavin and other heterocycle compounds as described by: O. S. Wolfbeis, Fiber Optic Chemical Sensors and Biosensors; O. S. Wolfbeis, Ed.; CRC Press: Boca Raton, Fla., 1991; Vol. 2; pp 19–53.

Yet another group of reagents includes metal-organic complexes of ruthenium, osmium, iridium, gold and platinum as described by: O. S. Wolfbeis, Fiber Optic Chemical Sensors and Biosensors; O. S. Wolfbeis, Ed.; CRC Press: Boca Raton, Fla., 1991; Vol. 2; pp 19–53, J. N. Demas, B. A. Degraff, P. B. Coleman, "Oxygen sensors based on luminescence quenching," Anal. Chem. 1999, 71, 793A–800A;J. N. Demas, B. A. DeGraff, "Design and applications of highly luminescent transition metal complexes," Anal. Chem. 1991, 63, 829A–837A; A. Mills, A. Lepre, B. R. Theobald, E. Slade, B. A. Murrer, "Use of luminescent gold compounds in the design of thin-film oxygen sensors," Anal. Chem. 1997, 69, 2842–2847; Potyrailo, R. A.; Hieftje, G. M., Use of the original silicone cladding of an optical fiber as a reagent-immobilization medium for intrinsic chemical sensors, Fresenius' J. Anal. Chem. 1999, 364, 32–40.

Yet another group of reagents includes solvatochromic dyes as extensively reviewed in, for example, C. Reichardt, *Chemical Reviews,* volume 94, pages 2319–2358 (1994). Preferred fluorescent solvatochromic dyes have a luminescence quantum yield of greater than about 0.01. Other characteristics of the dyes include positive and negative solvatochromism which corresponds to the bathochromic and hypsochromic shifts, respectively of the emission band with increasing solvent polarity. In addition to the solvent-induced spectral shifts of the emission spectra, some dyes exhibit the solvent-dependent ratio of emission intensities of two luminescence bands. One such solvatochromic dye is pyrene. Some examples of preferred solvatochromic dyes include 4-dicyanmethylene-2-methyl-6-(p-dimethylaminostyryl)-4 H-pyran (DCM; CAS Registry No. 51325-91-8); 6-propionyl-2-(dimethylamino)naphthalene (PRODAN; CAS Registry No. 70504-01-7); 9-(diethylamino)-5H-benzo[a]phenoxazin-5-one (Nile Red; CAS Registry No. 7385-67-3); phenol blue; stilbazolium dyes; coumarin dyes; ketocyanine dyes, including CAS Registry No. 63285-01-8; Reichardt's dyes including Reichardt's betaine dye (2,6-diphenyl-4-(2,4,6-triphenylpyridinio)phenolate; CAS Registry No. 10081-39-7); merocyanine dyes, including merocyanine 540 (CAS Registry No. 62796-23-0); so-called $\pi^*$ dyes, including N,N-dimethyl-4-nitroaniline (NDMNA; CAS Registry No.100-23-2) and N-methyl-2-nitroaniline (NM2NA; CAS Registry No.612-28-2); and the like. Applications of solvatochromic dyes for monitoring of moisture are described for example in Sadaoka, Y.; Matsuguchi, M.; Sakai, Y.; Murata, Y.-U., Optical humidity sensor using Reichardt's betain dye-polymer composites, *Chem. Lett* 1992, 53–56; Sadaoka, Y.; Sakai, Y.; Murata, Y., Optical humidity and ammonia gas sensors using Reichardt's dye-polymer composites, *Talanta* 1992, 39, 1675–1679; Potyrailo, R. A.; Hieftje, G. M., Use of the original silicone cladding of an optical fiber as a reagent-immobilization medium for intrinsic chemical sensors, *Fresenius' J. Anal. Chem.* 1999, 364, 32–40.

Yet another group of reagents includes colorimetric and luminescent acid-base and cationic reagents as extensively reviewed in, for example, Kolthoff, I. M. Acid-Base Indicators; The MacMillan Company: New York, 1937; Bacci, M.; Baldini, F.; Bracci, S., Spectroscopic behavior of acid-base indicators after immobilization on glass supports, Appl. Spectrosc. 1991, 45, 1508–1515; Sadaoka, Y.; Matsuguchi, M.; Sakai, Y.; Murata, Y.-U., Optical humidity sensing characteristics of Nafion-dyes composite thin films, Sens. Actuators B 1992, 7, 443–446; Sadaoka, Y.; Sakai, Y.; Murata, Y., Optical properties of cresyl violet-polymer composites for quantification of humidity and ammonia gas in ambient air, J. Mater. Chem. 1993, 3, 247–251; Zinger, B.; Shier, P., Spectroscopic studies of cationic dyes in Nafion, Preliminary investigation of a new sensor for hydrophilic contamination in organic solvents, Sens. Actuators B 1999, 56, 206–214; Haugland, R. P. Handbook of Fluorescent Probes and Research Chemicals; Molecular Probes: Eugene, Oreg., 1996. Some of these dyes are thymol blue, congo red, methyl orange, bromocresol green, methyl red, bromocresol purple, bromothymol blue, cresol red, phenolphthalein, SNAFL indicators, SNARF indicators, 8-hydroxypyrene-1, 3,6-trisulfonic acid, fluorescein and its derivatives, oregon green, and a variety of dyes mostly used as laser dyes including rhodamine dyes, styryl dyes, cyanine dyes, and a large variety of other dyes. These reagents may also be referred to as pH reagents. Yet another group of reagents includes oxygen-sensitive colorimetric reagents. Some reagents useful for colorimetric determinations of molecular oxygen are reviewed in Chemical Detection of Gaseous Pollutants; Ruch, W. E., Ed.; Ann Arbor Science Publishers: Ann Arbor, Mich., 1968. These include, among others, 2,4-diaminophenol dihydrochloride, manganous oxide, combination of manganous hydroxide and potassium iodide containing starch, ferrous salt in combination with methylene blue, reduced form of sodium anthraquinone-B-sulfonate, reduced form of ammonium anthraquinone-2-sulfonate, carbohydrate of Tschitschibabin, alkaline pyrogallol, and ammoniacal cuprous chloride. These and many other colorimetric reagents can be dispersed in a solid matrix, such as sol-gel, silica-gel and/or a polymer film, or dissolved in a suitable solvent.

Variation of the detectable property of a chemically sensitive film can be performed upon a change of refractive index of the film upon exposure to the material of interest, such as water vapor. Such moisture sensitive material can be a hydrogel. A hydrogel is a three dimensional network of hydrophilic polymers which have been tied together to form water-swellable but water insoluble structures. The term hydrogel is to be applied to hydrophilic polymers in a dry state (xerogel) as well as in a wet state as described in U.S. Pat. No. 5,744,794.

There are a number of methods that may be used to tie these hydrogels together. First, tying via radiation or radical cross-linking of hydrophilic polymers, examples being poly(acrylic acids), poly(methacrylic acids), poly(hydroxyethylmethacrylates), poly(glyceryl methacrylate), poly(vinyl alcohols), poly (ethylene oxides), poly(acrylamides), poly(N-acrylamides), poly(N,N-dimethylaminopropyl-N'-acrylamide), poly(ethylene imines), sodium/potassium poly(acrylates), polysacharides e.g. xanthates, alginates, guar gum, agarose etc., poly(vinyl pyrrolidone) and cellulose based derivatives. Second, tying via chemical cross-linking of hydrophilic polymers and monomers, with appropriate polyfunctional monomers, examples include poly(hydroxyethylmethacrylate) cross-linked with suitable agents, the copolymerisation of hydroxyethylmethacrylate monomer with dimethacrylate ester crosslinking agents, poly(ethylene oxide) based polyurethanes prepared through the reaction of hydroxyl-terminated poly (ethylene glycols) with polyisocyanates or by the reaction with diisocyanates in the presence of polyfunctional monomers such as triols, and cellulose derivates cross-linked with dialdehydes, diepoxides and polybasic acids. Third, tying via incorporation of hydrophilic monomers and polymers into block and graft copolymers, examples being block and graft copolymers of poly(ethylene oxide) with suitable polymers, poly(vinyl pyrrolidone)-co-polystyrene copolymers, polyurethanes and polyurethaneureas and polyurethaneureas based on poly (ethylene oxide), polyurethaneureas and poly(acrylonitrile)-co-poly(acrylic acid) copolymers, and a variety of derivatives of poly(acrylontriles), poly(vinyl alcohols) and poly(acrylic acids). Fourthly molecular complex formation between hydrophilic polymers and other polymers, examples being poly(ethylene oxides) hydrogel complexes with poly(acrylic acids) and poly(methacrylic acids). Last, tying via entanglement cross-linking of high molecular weight hydrophilic polymers, examples being hydrogels based on high molecular weight poly(ethylene oxides) admixed with polyfunctional acrylic or vinyl monomers.

Examples of applications of these materials are in Michie, W. C., Culshaw, B., Konstantaki, M.; McKenzie, I., Kelly, S., Graham, N. B., Moran, C., Distributed pH and water detection using fiber-optic sensors and hydrogels, J. Lightwave Technol. 1995, 13, 1415–1420; Bownass, D. C.; Barton, J. S.; Jones, J. D. C., Serially multiplexed point sensor for the detection of high humidity in passive optical networks, Opt. Lett. 1997, 22, 346–348; Michie, W. C.; Graham, N. B.; Cuishaw, B.; Gardiner, P. T.; Moran, C., Apparatus for detecting aqueous environments, U.S. Pat. No. 5,744,794 (1995).

Chemically sensitive reagents are incorporated into a sensor layer formed from film-forming polymeric and/or inorganic material. The material for the sensor layer may affect the detection properties such as selectivity, sensitivity, and limit of detection. Thus, suitable material for the sensor layer is selected from polymeric and/or inorganic material capable of providing required response time, material of interest permeability, material of interest solubility, degree of transparency and hardness, and other similar characteristics relevant to the material of interest and the desired barrier property to be analyzed.

In general, the sensor layer has a response time in the range of about 1 microsecond 60 minutes, particularly in the range of about 1 millisecond 10 minutes, and more particularly in the range of about 1 second 1 minute.

In general, the permeability of the barrier coating to material of interest is in the range of about 0.0001 100 $cm^3$ mm/$m^2$ day atm, particularly in the range of about 0.001 10 $cm^3$ mm/$m^2$ day atm, and more particularly in the range of about 0.005 5 $cm^3$ mm/$m^2$ day atm.

In general, the sensor layer has a thickness in the range of about 0.001 micrometer 1000 micrometers, particularly from about 0.01 micrometer 500 micrometers, and more particularly in the range of about 0.1 micrometer 200 micrometers.

For example, in general polymers that can be used as matrices for oxygen, water vapor, and other sensors can be divided into several classes as described by: S. A. Stern, B. Krishnakumar, S. M. Nadakatti, Physical Properties of Polymers Handbook; J. E. Mark, Ed.; AIP Press: New York, 1996; pp 687–700. Such classes include polyolefins, vinyl and vinylidene polymers, natural and synthetic rubbers, polyesters, polycarbonates, cellulose derivatives, fluoropolymers, polyorganosiloxanes, polynitriles, polyamides, polyimides, polyurethanes, polyoxides, polysulfones, polyacetylenes, polyacrylics.

More detailed examples of polymers are described by Freud, M. S.; Lewis, N. S., "A chemically diverse conducting polymer-based "electronic nose"", Proc. Natl. Acad. Sci. USA 1995, 92, 2652–2656; Albert, K. J.; Lewis, N. S.; Schauer, C. L.; Sotzing, G. A.; Stitzel, S. E.; Vaid, T. P.; Walt, D. R., "Cross-reactive chemical sensor arrays,"Chem. Rev. 2000, 1000, 2595–2626; Grate, J. W.; Abraham, H.; McGill, R. A. In "Handbook of Biosensors and Electronic Noses. Medicine, Food, and the Environment" E. Kress-Rogers, Ed.; CRC Press: Boca Raton, Fla., 1997; pp 593–612; Grate, J. W.; Abraham, M. H., "Solubility interactions and the design of chemically selective sorbent coatings for chemical sensors and arrays," Sens. Actuators B 1991, 3, 85–111; U.S. Pat. Nos. 6,010,616 and 6,093,308.

They include: conducting polymers such as poly(anilines), poly(thiophenes), poly(pyrroles), poly(acetylenes), etc.; main-chain carbon polymers such as poly(dienes), poly(alkenes), poly(acrylics), poly(methacrylics), poly(vinyl ethers), poly (vinyl thioethers), poly(vinyl alcohols), poly(vinyl ketones), poly(vinyl halides), poly (vinyl nitriles), poly(vinyl esters), poly(styrenes), poly (arylenes), etc.; main-chain acyclic heteroatom polymers such as poly(oxides), poly(carbonates), poly(esters), poly (anhydrides), poly(urethanes), poly(sulfonates), poly (siloxanes), poly(sulfides), poly(thioesters), poly(sulfones), poly(sulfonamides), poly(amides), poly(ureas), poly (phosphazenes), poly(silanes), poly(silazanes), etc.; and, main-chain heterocyclic polymers such as poly (benzoxazoles), poly(oxadiazoles), poly (benzothiazinophenothiazines), poly(benzothiazoles), poly (pyrazinoquinoxalines), poly(pyromellitimides), poly (quinoxalines), poly(benzimidazoles), poly(oxindoles), poly (oxoisoindolines), poly(dioxoisoindolines), poly(triazines), poly(pyridazines), poly(piperazines), poly(pyridines), poly (piperidines), poly(triazoles), poly (pyrazoles), poly (pyrrolidines), poly(carboranes), poly(oxabicyclononanes), poly (dibenzofurans), poly(phthalides), poly(acetals), poly (anhydrides), carbohydrates, etc.

Other types of matrices include: the copolymers, polymer blends, and physical mixtures or polymers with additives such as organic and inorganic pigments, conducting, semiconducting, and non-conducting particles; inorganic sol-gel materials produced by condensation reactions, these materials can be doped with organic components; and polyelectrolytes, such as high-density polyethylene grafted with poly(styrenesulfonic acid), Nafion, and others.

The chemically sensitive layer is formed by incorporating the chemically sensitive reagents into the polymeric and/or inorganic material for the sensor layer. Incorporation of the chemically sensitive reagents may be carried out by dissolving a chemically sensitive reagent in a solution or suspension of polymeric and/or inorganic material in a suitable solvent and then the resultant solution or suspension is applied to a substrate to form a chemically sensitive layer using various methods using thin-film deposition techniques that are explained below. An optional step is curing or condensation reaction. Solvents can be either polar or non polar, including but not limited to water, ethanol, methanol, acetone, chloroform, toluene, benzene, and hexane.

Another method for incorporation of chemically sensitive reagents includes dissolving a chemically sensitive reagent in a suitable solvent and immersing a polymer or/and inorganic film into the reagent solution. The solvent is sorbed into or onto the film and some of the chemically sensitive reagent molecules become trapped in the film. Upon drying, curing, or condensation, the solvent is removed while the chemically sensitive reagent remains trapped in the film. Covalent attachment of the reagent to the film is also possible.

For example, for oxygen permeability, a suitable chemically sensitive layer includes a polymeric material, such as polyvinyl chloride (PVC), polystyrene (PS), polycarbonate (PC), poly(methyl methacrylate) (PMMA), PMMA/CAB blends, poly(1-trimethylsilyl-1-propyne), fluoro-polymer such as poly(styrene-co-trifluoroethyl-methacrylate) (poly-styrene-co-TFEM) and other fluoropolymers, sol-gels doped with an oxygen sensitive reagent, such as platinum or palladium porphyrins, such as platinum(II) octaethylporphyrin (Pt-OEP) and palladium(II) octaethylporphyrin (Pd-OEP); metal-organic complexes of ruthenium, osmium, iridium, gold and platinum; or other known similar materials.

Other suitable example of chemically sensitive layers include polycyclic aromatic hydrocarbons such as pyrene, pyrenebutyric acid, fluoranthene, decacyclene, diphenylanthracene, and benzo(g,h,l)perylene, immobilized in a cellulose acetate butyrate (CAB), silicones, silicone blends, silicone copolymers, combinations thereof, and other similar materials.

Still other suitable example of chemically sensitive layers include solvatochromic, acid-base, and cationic dyes such as pyrene, 4-dicyanmethylene-2-methyl-6-(p-dimethylaminostyryl)-4H-pyran; 6-propionyl-2-(dimethylamino) naphthalene; 9-(diethylamino)-5H-benzo[a]phenoxazin-5-one; phenol blue; stilbazolium dyes; coumarin dyes; ketocyanine dyes, Reichardt's dyes; merocyanine dyes, thymol blue, congo red, methyl orange, bromocresol green, methyl red, bromocresol purple, bromothymol blue, cresol red, phenolphthalein, SNAFL dyes, SNARF dyes, 8-hydroxypyrene-1,3,6-trisulfonic acid, fluorescein and its derivatives, oregon green, and a variety of dyes mostly used as laser dyes including rhodamine dyes, styryl dyes, cyanine dyes, and a large variety of other dyes immobilized in an inorganic material such as sol-gel matrix or in a polymeric material, such as polyvinyl chloride (PVC), polystyrene (PS), polycarbonate (PC), poly (methyl methacrylate) (PMMA), PMMA/CAB blends, fluoro-polymer such as poly (styrene-co-trifluoroethyl-methacrylate) (poly-styrene-co-TFEM) and other fluoropolymers, cation exchange membranes such as Nafion, and others, combinations thereof, and other similar materials.

For example, the sensor layer may be exposed to varying concentrations of oxygen, water vapor, other inorganic and organic vapors and gases and their combinations at different ratios. For example, in measurements of oxygen barrier property, oxygen concentrations range from 0 to 100% by volume. Partial pressure of oxygen can range from 0 to 1 atmosphere. However, in order to accelerate penetration of oxygen, the partial pressure can be increased higher than 1 atmosphere and, depending on the equipment used, can be, for example 10 or 100 atmosphere or even higher.

In measurements of moisture barrier property, water vapor concentrations range from 0 to 100 % by volume. Partial pressure of water vapor can range from 0 to 1 atmosphere. However, in order to accelerate penetration of water vapor, the partial pressure can be increased higher than 1 atmosphere and, depending on the equipment used, can be, for example 10 or 100 atmosphere or even higher.

The sensor layer may be exposed first to the atmosphere at which the coating deposition was performed, and then to nitrogen, oxygen, water vapor, or other inorganic or organic vapor or gas or their combinations at different ratios.

The change in the absorbance, refractive index, luminescence intensity, or lifetime of the regions of the sensor materials may be measured using a described system.

In one embodiment, the correlation of detection to impacted barrier coatings is determined via use of optical time-of-flight chemical detection (OTOF), otherwise known as spatially resolved mapping. Upon measurements of back-reflected light, this technique is known as optical time domain reflectometry (OTDR). With this technique, a pulse of light is periodically launched into the waveguide, and analytical information is derived from the amplitude and/or other characteristics of the returned portion of the light. In one embodiment, the amplitude of the returned light is modulated by variations in analyte concentration along the waveguide that occur due to penetration of a material of interest through a barrier coating applied to the waveguide. In particular, in one embodiment, information about the location of the variation in analyte concentration is obtained from the measured time delay between the launched and returned pulses of light.

To address drawbacks with this technique when absorbance of material of interest is detected in the UV-IR spectral ranges or when chemically sensitive colorimetric dyes are used with the basic OTOF sensing of this method, including low levels of detected backscatter signal, an embodiment of the present invention also includes use of absorption-modulated luminescence detection which raises signal levels of absorption-based sensors to levels found in luminescence-based sensors. With this approach, the luminescence intensity of an immobilized analyte-insensitive fluorophore is monitored by an analyte sensitive indicator as a function of absorbance caused by a second immobilized analyte-insensitive fluorophore.

Another potential drawback relating to OTOF sensing using detection of absorbance of material of interest in the UV-IR spectral ranges or using chemically sensitive colorimetric dyes and/or statically quenched fluorophores is the accumulative analyte-induced light attenuation. A local increase in evanescent-wave absorbance by an immobilized reagent or absorbance of the material of interest in the UV-IR spectral ranges leads to a drop in light intensity available for propagation farther down the waveguide. The dynamic range can therefore be limited by high analyte concentrations along the waveguide. To address this limitation, dynamically quenched fluorophores are used with sensing. Sensors based on immobilized dynamically quenched fluorophores do not exhibit a change in attenuation coefficient upon exposure to a quencher. See, e.g., R. A. Potyrailo and G. M. Hieftge, "Spatially Resolved Analyte Mapping With Time-Of-Flight Optical Sensors," *Trends. Anal. Chem.*, vol. 17, 593–604 (1998).

The chemically sensitive layer and the barrier coatings are deposited on the waveguide using a number of methods and systems, such as by spraying, drawing, dipping and otherwise depositing the materials on the waveguide. A length of waveguide material is coatable with a chemically sensitive layer, and the chemically sensitive layer is then coatable with adjacent layers of barrier coatings, such that an array of barrier coatings is formed upon the length of the waveguide material.

Thin-film deposition techniques in combination with physical masking techniques or photolithographic techniques can be used to apply a barrier coating layer onto a sensor layer. Such thin-film deposition techniques can generally be broken down into the following four categories: evaporative methods, glow discharge processes, gas-phase chemical processes, and liquid-phase chemical techniques. Included within these categories are, for example, sputtering techniques, spraying techniques, laser ablation techniques, electron beam or thermal evaporation techniques, ion implantation or doping techniques, chemical vapor deposition techniques, as well as other techniques used in the fabrication of integrated circuits. All of these techniques can be applied to deposit highly uniform layers, i.e., thin-films, of the various coating materials on selected regions on the sensor layer. Moreover, by adjusting the relative geometries of the masks, the delivery source and/or the substrate, such thin-film deposition techniques can be used to generate uniform gradients at each reaction region on the substrate or, alternatively, over all of the reaction regions on the substrate. For an overview of the various thin-film deposition techniques which can be used in the methods of the present invention, see, for example, Ballantine, D. S., Jr.; White, R. M.; Martin, S. J.; Ricco, A. J.; Frye, G. C.; Zellers, E. T.; Wohltjen, H. "Acoustic Wave Sensors: Theory, Design, and Physico-Chemical Applications", Chapter 6, Academic Press: San Diego, Calif., 1997; which are incorporated herein by reference for all purposes.

In one embodiment, thin-films of the various barrier coating materials can be deposited onto the sensor layer using evaporative methods in combination with physical masking techniques. Generally, in thermal evaporation or vacuum evaporation methods, the following sequential steps take place: (1) a vapor is generated by boiling or subliming a target material; (2) the vapor is transported from the source to a substrate; and (3) the vapor is condensed to a solid film on the substrate surface. Evaporants, i.e., target materials, which can be used in the evaporative methods cover an extraordinary range of chemical reactivities and vapor pressures and, thus, a wide vary of sources can be used to vaporize the target materials. Such sources include, for example, resistance-heated filaments, electron beams; crucible heated by conduction, radiation or rf-inductions; and arcs, exploding wires and lasers. In preferred embodiments of the present invention, thin-film deposition using evaporative methods is carried out using lasers, filaments, electron beams or ion beams as the source. Successive rounds of deposition, through different physical masks, using evaporative methods can be used to generate a library or array of barrier coatings on a sensory layer for detection of defects in the barrier coatings in combinatorial discovery of coating materials.

Molecular Beam Epitaxy (MBE) is an evaporative method that can be used to grow epitaxial thin-films. In this method, the films are formed on single-crystal substrates by slowly evaporating the elemental or molecular constituents of the film from separate Knudsen effusion source cells (deep crucibles in furnaces with cooled shrouds) onto substrates held at temperatures appropriate for chemical reaction, epitaxy and re-evaporation of excess reactants. The Knudsen effusion source cells produce atomic or molecular beams of relatively small diameter which are directed at the heated substrate, usually silicon or gallium arsenide. Fast shutters are interposed between the source cells and the substrates. By controlling these shutters, one can grow superlattices with precisely controlled uniformity, lattice match, composition, dopant concentrations, thickness and interfaces down to the level of atomic layers.

In addition to evaporative methods, thin-films of the various barrier coating materials can be deposited onto the sensor layer or onto the substrate using glow-discharge processes in combination with physical masking techniques. The most basic and well known of these processes is sputtering, i.e., the ejection of surface atoms from an electrode surface by momentum transfer from bombarding ions to surface atoms. Sputtering or sputter-deposition is a term used by those of skill in the art to cover a variety of processes, all of which can be used in the methods of the present invention. One such process is RF/DC Glow Discharge Plasma Sputtering. In this process, a plasma of energized ions is created by applying a high RF or DC voltage between a cathode and an anode. The energy ions from the plasma bombard the target and eject atoms which are then deposited on a substrate, a sensor layer. Ion-Beam Sputtering is another example of a sputtering process which can be used to deposit thin-films of the various barrier coating materials on a substrate. Ion-Beam Sputtering is similar to the foregoing process except the ions are supplied by an ion source and not a plasma. It will be apparent to one of skill in the art that other sputtering techniques (e.g., diode sputtering, reactive sputtering, etc.) and other glow-discharge processes can be used in the methods of the present invention to deposit thin-films on a substrate and a sensor layer. Successive rounds of deposition, through different physical masks, using sputtering or other glow-discharge techniques, can be used to generate an array or library of barrier coatings on a sensor layer for detection of defects in the barrier coating for use of combinatorial discovery of coating materials.

In addition to evaporative methods and sputtering techniques, thin-films of the various barrier coating materials can be deposited onto the sensor layer or onto the substrate using Chemical Vapor Deposition (CVD) techniques in combination with physical masking techniques. CVD involves the formation of stable solids by decomposition of gaseous chemicals using heat, plasma, ultraviolet, or other energy source, or a combination of energy sources. Photo-Enhanced CVD, based on activation of the reactants in the gas or vapor phase by electromagnetic radiation, usually short-wave ultraviolet radiation, and Plasma-Enhanced CVD, based on activation of the reactants in the gas or vapor phase using a plasma, are two particularly useful chemical vapor deposition techniques. Successive rounds of deposition, through different physical masks, using CVD technique can be used to generate an array or library of barrier coatings on a sensor layer for detection of defects in the barrier coating in combinatorial discovery of coating materials.

In addition to evaporative methods, sputtering and CVD, thin-films of the various reactants can be deposited onto the sensor layer or onto the substrate using a number of different mechanical techniques in combination with physical masking techniques. Such mechanical techniques include, for example, spraying, spinning, dipping, draining, flow coating, roller coating, pressure-curtain coating, brushing, etc. Of these, the spray-on and spin-on techniques are particularly useful. Sprayers which can be used to deposit thin-films include, for example, ultrasonic nozzle sprayers, air atomizing nozzle sprayers and atomizing nozzle sprayer. In ultrasonic sprayers, disc-shaped ceramic piezoelectric transducers covert electrical energy into mechanical energy. The transducers receive electrical input in the form of a high-frequency signal from a power supply that acts as a combination oscillator/amplifier. In air atomizing sprayers, the nozzles intermix air and liquid streams to produce a completely atomized spray. In atomizing sprayers, the nozzles use the energy from a pressurized liquid to atomize the liquid and, in turn, produce a spray. Successive rounds of deposition, through different physical masks, using mechanical techniques, such as spraying, can be used to generate an array or library of barrier coatings on a circular sensor layer for detection of transport properties of barrier coatings in combinatorial discovery of coating materials.

The barrier coating suitably has a thickness from 0.1 nm to 100 micrometers, particularly from 1 nm to 10 micrometers, and more particularly from 10 nm to 5 micrometers.

Figure 3:
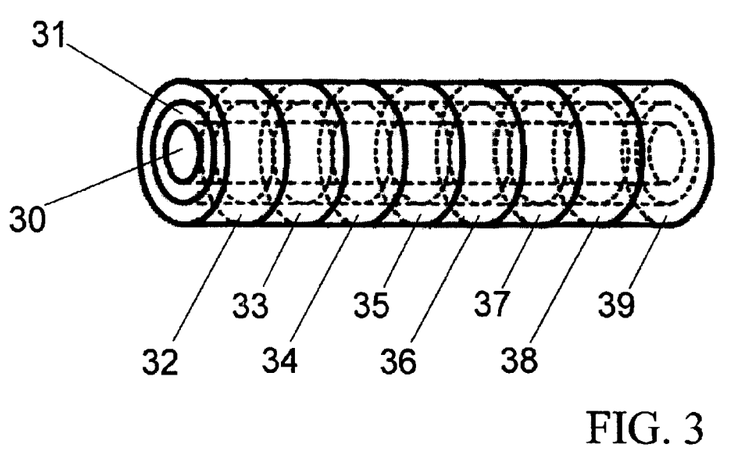
FIG. 3 presents a waveguide structure for measurements of barrier properties of an array of coatings in accordance with an embodiment of the present invention.

In combinatorial discovery of coating materials for applications as barrier and other types of coatings, the rapid evaluation of permeability of coatings is needed. To provide methods and devices for measurements of barrier properties of multiple coatings with the reduced errors associated with the edge effects, in an embodiment of the present invention, an array of barrier coatings is deposited onto the waveguide structure, as shown in FIG. 3. FIG. 3 presents a waveguide 30 having an outer side surface coated with a chemically sensitive layer 31 and an array of barrier coatings 32, 33, 34, 35, 36, 37, 38, 39. Preferably, each of the elements of the array of barrier coatings has a known predetermined different composition such that the measured variations in barrier coating performance may be correlated to the known variations in the coating composition. The array of barrier coatings are adjacently positioned lengthwise along the waveguide such that there is no space between the coatings, thereby eliminating edge effects in all three dimensions. For example, the barrier coatings may include a single coating having a varying composition lengthwise along the waveguide. Such a barrier coating may be formed, for example, by simultaneously depositing different combinations of different materials lengthwise along the waveguide, where a given material composition forming a barrier coating is mappable to a given position. Alternatively, if there is space between the array of coatings, then the edge effects are eliminated in two dimensions. An array of barrier coating may also include situations when coating thickness is introduced as a variable parameter. An array of barrier coating may also include situations when processing and reaction conditions of coating fabrication are introduced as variable parameters.

Figure 4:
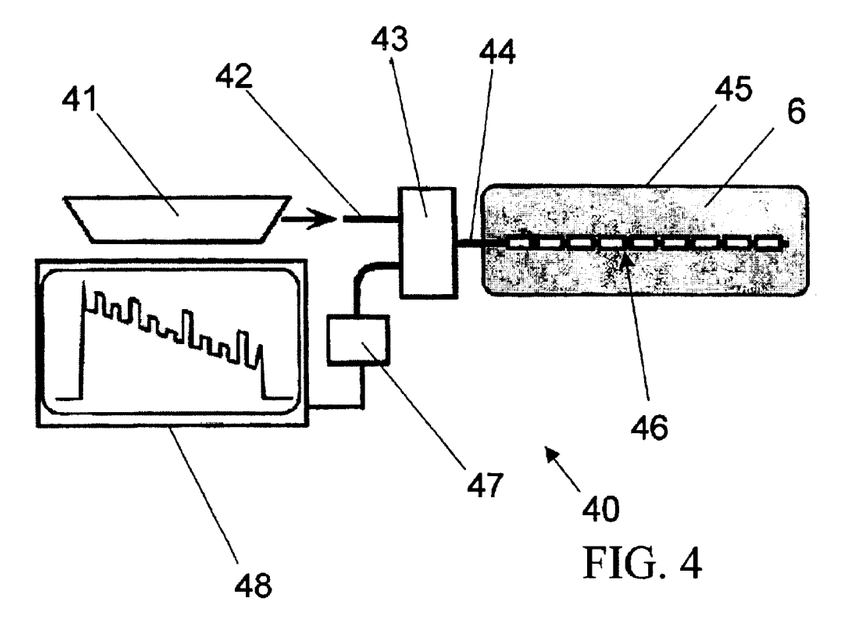
FIG. 4 shows an optical system for spatially resolved measurements of barrier properties of an array of coatings toward a vapor of interest in accordance with an embodiment of the present invention.

FIG. 4 shows one embodiment of an optical system 40 for spatially resolved measurements of barrier properties of an array of coatings 46 with regard to a material of interest 6. The system 40 performs the measurements utilizing the spatially resolved capability provided by an optical time-of-flight detection technique. FIG. 4 presents a light source 41 that pulses a wave of light through an optical fiber input 42 and a fiber optic coupler 43 into a chemically sensitive waveguide 44. Waveguide 44 has a structure similar to that of waveguide 30 (see FIG. 3), including a chemically sensitive layer and an array of barrier coatings 46. Although shown as spaced apart along the length of the waveguide 44, the array of barrier coatings 46 may be positioned without any space in between each coating to eliminate edge effects in two or three dimensions. The array of barrier coatings 46 is exposed to one or more material(s) of interest 6 contained within a gas cell 45. A detector 47, such as a photodetector for measuring the pulsed light wave, is connected to the waveguide 44 to measure the effects on each barrier coating to the exposure to the material of interest 6. The system 40 may also include a display 48 connected to the detector 47 for graphically depicting the measurements of the detector. The display includes, for example, a personal computer (PC), a microcomputer, a minicomputer, a mainframe computer, or other device having a processor.

For example, the light source 41 may include a pulsed laser, or other suitable wave source such as those listed in the following Table 1.

TABLE 1

| Useful Light/Wave Sources | |
|---|---|
| Source | Spectral range of emission (nm) |
| Diode lasers | different diode lasers cover ranges from 400 to 1500 nm |
| Light emitting diodes | different diodes cover ranges from 370 to 1500 |
| Excimer lasers | 157, 193, 248, 308, 351 |
| Nitrogen laser | 337 |
| Nd: YAG laser | fundamental-1064, frequency doubled-532, tripled-355, quadrupled-266 |
| Ti: Sapphire laser | 72–1000, frequency doubled 360–500 |
| Dye lasers | 360–990, frequency doubled 235 to 345 |

In an embodiment of the present invention, the waveguide includes, for example, a chemically sensitive layer of an oxygen sensitive material if oxygen barrier properties are of interest.

In another embodiment of the present invention, the waveguide includes a chemically sensitive layer of a moisture sensitive material if moisture barrier properties are of interest.

In an embodiment of the present invention, the waveguide includes, for example, a chemically sensitive layer of an oxygen and moisture sensitive material if combined oxygen and moisture barrier properties are of interest.

Other fluids, gases, vapors, or liquids are measurable by incorporating other chemical reagents into the material of the chemically sensitive layer.

The waveguide is preferably impermeable to the material of interest. Examples of waveguides of such geometry, known as optical fibers, are shown in Table 2.

TABLE 2

Useful optical fiber waveguides

| Supplier | Fiber core material (and diameters, microns) | Fiber cladding materials (and diameters, microns) |
|---|---|---|
| Polymicro Technologies, Inc., Phoenix, Az | silica (125, 200, 400, 500, 700) | hard polymer (140, 220, 420, 520, 740) |
| | silica (300, 400, 600, 800) | silicone (450, 500, 700, 900) |
| Fiberguide Industries, Inc., Stirling, NJ | silica (200, 300, 400, 600, 800, 1000, 1500, 2000) | silicone (300, 400, 500, 700, 900, 1100, 1650, 2150) |
| 3M Specialty Fibers, West Haven, CT | silica (125, 200, 300, 400, 600, 800, 1000, 1500) | hard polymer (140, 230, 330, 430, 630, 830, 1035, 1550) |
| | silica (200, 400, 600, 1000) | silicone (380, 600, 830, 1400) |

The original fiber cladding can be chemically modified with a chemically sensitive reagent of interest as described by Potyrailo, R. A.; Hieftje, G. M., "Use of the original silicone cladding of an optical fiber as a reagent-immobilization medium for intrinsic chemical sensors," *Fresenius' J. Anal. Chem.* 1999, 364, 32–40. Also, the fiber cladding can be removed using methods described in a Product Catalog "3M Power-Core Fiber Products" from Specialty Fibers, West Haven, Conn. and in Ruddy, V.; MacCraith, B. D.; Murphy, J. A., "Evanescent wave absorption spectroscopy using multimode fibers," *J. Appl. Phys.* 1990, 67, 6070–6074, where cladding materials can be removed by applying available solvents.

The chemically sensitive material (reagent in a suitable matrix) can be deposited as described above.

For detection of the wave back-propagating in the waveguide, several possible detection system configurations can be used. In one detection system, light from a pulsed laser is launched into the waveguide through a beamsplitter by means of a lens. Backpropagated signal is collected with the same lens, redirected through the beamsplitter, and focused with another lens onto the entrance slit of a monochromator. Signal is monitored with a photomultiplier tube. A small portion of the laser light is directed to a fast photodiode by a mirror. The returned waveforms were recorded with a digitizing oscilloscope; the oscilloscope is triggered by the output from the fast photodiode. Each monitored waveform is averaged over several laser pulses, transferred to a computer, and analyzed using commercial software packages. Software packages for signal analysis are LabVIEW from National Instruments (Austin, Tex.), Matlab (The Mathworks Inc., Natick, Mass.), or others.

In addition to the cylindrical geometry for the embodiment shown in FIG. 3, the waveguide may be of any cross-section or shape such that the coating continuously covers the outer surface, except for at least one end, or where non-coated surfaces are arranged on a non-permeable substrate. Measurements of barrier properties are performable on different regions of the waveguides using optical time-of-flight detection methods, for example, as shown in FIG. 4, or using multiplexing techniques where each coating is deposited on a different waveguide.

In addition to the application of indirect sensing methods that employ a chemically sensitive reagent to flag the presence and concentration of an optically inactive vapor, a variety of direct spectroscopic techniques are capable of being utilized. These optionally include, for example, ultraviolet (UV), near-infrared (near-IR), mid-IR methods, and luminescence and Raman spectroscopies. For example, permeation of water vapor through a barrier coating deposited onto a waveguide is measurable in the near- and mid-IR spectral ranges. Also, pulsed excimer lasers emitting in the vacuum UV range can be used to probe for absorption of oxygen reaching the waveguide.

Thus, in summary, methods and devices have been disclosed for measuring barrier properties of a barrier coating or coating arrays where each barrier coating has a small cross section. To reduce the edge effects in the measurements of barrier properties, measurements are made using a waveguide structure coated with a chemically sensitive layer and an array of barrier coatings. The coated waveguide is exposed to a material of interest to produce an analyzable variation in the chemically sensitive layer to detect an impact on the barrier coatings. In one variation, a propagated wave, such as pulsed light, is propagated within the waveguide structure, and the impact on the propagated wave are detected and correlated to a value of a barrier property for each of the array of barrier coatings.

Example embodiments of the present invention have now been described. It will be appreciated that these examples are merely illustrative of the invention. Many variations and modifications will be apparent to those skilled in the art.

What is claimed is:

1. A device for measurement of barrier properties of barrier coatings, the device comprising:
   at least one waveguide having an external surface;
   a chemically sensitive layer disposed about the external surface of the at least one waveguide, the chemically sensitive layer responsive to a material of interest;
   a predefined number of barrier coatings deposited onto the chemically sensitive layer, each of the barrier coatings having a corresponding barrier property with respect to the material of interest;
   a light source operable to propagate a wave within the at least one waveguide;
   a detector operable to measure impacts associated with the propagated wave, the impacts associated with the respective barrier property of each of the predefined number of barrier coatings; and
   a correlator for correlating the measured impact with a value of the barrier property for each of the predefined number of barrier coatings.

2. The device of claim 1, wherein the predefined number of barrier coatings is one coating.

3. The device of claim 1, wherein the predefined number of barrier coatings is a plurality of coatings comprising a combinatorial array.

4. The device of claim 1, wherein the impacts are associated with a detected wave that is forward-propagated.

5. The device of claim 1, wherein the impacts are associated with a detected wave that is back-propagated.

6. The device of claim 1, wherein the at least one waveguide comprises an optical fiber and wherein each of the plurality of barrier coatings extend circumferentially about the waveguide in a spaced apart relationship.

7. The device of claim 6, wherein the at least one waveguide comprises a plurality of waveguides, wherein one of the plurality of barrier coatings is deposited on a corresponding one of the plurality of waveguides.

8. The device of claim 1, wherein the at least one waveguide comprises an optical fiber and wherein each of the plurality of barrier coatings extend circumferentially about the at least one waveguide and are adjacently positioned lengthwise along the waveguide such that there is no space between the coatings.

9. The device of claim 8, wherein the at least one waveguide comprises a plurality of waveguides, wherein one of the plurality of barrier coatings is deposited on a corresponding one of the plurality of waveguides.

10. The device of claim 1, wherein the plurality of barrier coatings each have a different predetermined parameter and a predetermined location lengthwise along the waveguide.

11. The device of claim 10, wherein the predetermined parameter is selected from the group consisting of composition, thickness, and coating preparation and/or storing and/or application conditions.

12. The device of claim 1, wherein the impacts measured by the detector is selected from the group consisting of an amplitude, a frequency, a polarization state, a phase, a temporal property, and combinations thereof.

13. The device of claim 1, wherein the barrier property comprises permeability.

14. The device of claim 1, wherein the chemically sensitive layer comprises a fluorophore.

15. The device of claim 1, wherein the chemically sensitive layer comprises a colorimetric reagent.

16. The device of claim 1, wherein the chemically sensitive layer comprises a polymeric material.

17. The device of claim 1, wherein the chemically sensitive layer comprises an inorganic material.

18. The device of claim 1, wherein the chemically sensitive layer comprises a sol-gel material.

19. The device of claim 1, wherein the predetermined number of barrier coatings comprise inorganic materials.

20. The device of claim 1, wherein the predetermined number of barrier coatings comprise organic materials.

21. The device of claim 1, wherein the predetermined number of barrier coatings comprise organic and inorganic materials.

22. The device of claim 1, wherein the predetermined number of barrier coatings are selected from the group consisting of oxides, nitrides and oxinitrides of silicon, aluminum, zinc, boron and other metals, ceramics, polyvinyl alcohol, ethylene vinyl alcohol copolymers, polyvinyl dichloride, different types of nylon, acrylics, cellophane, silicones, polyethylene terephtalate, PVC, PCTFE, polypropylene, sol-gels, and combinations thereof.

23. The device of claim 1, wherein the at least one waveguide, the chemically sensitive layer coating, and the predetermined number of barrier coatings comprise a waveguide structure; and the device further comprises a cell for containing the waveguide structure and the material of interest.

24. The device of claim 1, wherein the wave propagated by the light source further comprises a pulsed wave associated with a given time, and wherein the correlator includes a processor for determining a variation between the pulsed wave and the impacted wave and for correlating the determined variation with one of the plurality of barrier coatings based on the given time of the pulsed wave.

25. The device of claim 1, wherein the material of interest is selected from the group consisting of oxygen, water, water vapor, organic and inorganic vapors and combinations thereof.

26. The device of claim 1, wherein the impacts on the propagated wave are associated with a change in a chemically sensitive layer characteristic selected from the group consisting of absorption spectrum, refractive index, luminescence intensity, luminescence lifetime, luminescence spectrum and combinations thereof.

27. The device of claim 1, wherein the chemically sensitive layer comprises a thin film having a thickness in the range of about 0.05 to about 1000 micrometers.

28. The device of claim 1, wherein each of the plurality of barrier coatings comprises a thin film having a thickness in the range of about 0.1 nanometers to about 100 micrometers.

29. The device of claim 1, wherein the propagated wave produced by the light source has a spectral range of emission from about 150 nanometers to about 2500 nanometers.

30. A device for measurement of barrier properties of barrier coatings, the device comprising:
   at least one waveguide extending lengthwise and having an external surface;
   a chemically sensitive layer disposed about the circumference of the external surface of at least a portion of the at least one waveguide, the chemically sensitive layer responsive to a material of interest;
   a plurality of barrier coatings deposited onto the chemically sensitive layer such that each coating extends circumferentially about the at least one waveguide, each of the barrier coatings having a corresponding barrier property with respect to the material of interest;
   a light source operable to propagate a pulsed wave associated with a given time within the at least one waveguide;
   a detector operable to measure impacts associated with the propagated wave and associated with the respective barrier property of each of the plurality of barrier coatings; and
   a processor for determining a value of the barrier property associated with the measured impact and for correlating the value of the barrier property with each of the plurality of barrier coatings.

31. The device of claim 30, wherein the at least one waveguide comprises an optical fiber and wherein each of the plurality of barrier coatings extend circumferentially about the waveguide and are adjacently positioned lengthwise along the waveguide such that there is no space between the coatings.

32. The device of claim 30, wherein the impacts on the propagated wave measured by the detector is selected from the group consisting of an amplitude, a frequency, a polarization state, a phase, a temporal property, and combinations thereof.

33. The device of claim 30, wherein the barrier property comprises permeability.

34. The device of claim 30, wherein the at least one waveguide, the chemically sensitive layer coating, and the plurality of barrier coatings comprise a waveguide structure; and the device further comprises a cell for containing the waveguide structure and the material of interest.

35. The device of claim 30, wherein the material of interest is selected from the group consisting of oxygen, moisture, water vapor, organic and inorganic vapors and combinations thereof.

36. The device of claim 30, wherein the impacts on the propagated wave are associated with a change in a chemically sensitive layer characteristic selected from the group consisting of absorption spectrum, refractive index, luminescence intensity, luminescence lifetime, luminescence spectrum and combinations thereof.

37. The device of claim 30, wherein the chemically sensitive layer comprises a polymeric or inorganic or composite material.

38. The device of claim 30, wherein the chemically sensitive layer comprises a polymeric material having a sufficient combination of response time, material of interest permeability, material of interest solubility, and degree of transparency and hardness relative to the material of interest and the analyzed barrier property.

39. The device of claim 30, wherein the chemically sensitive layer comprises a dynamically quenched luminescent reagent.

40. The device of claim 30, wherein the chemically sensitive layer comprises a statically quenched luminescent reagent.

41. The device of claim 30, wherein the chemically sensitive layer comprises a colorimetric reagent.

42. The device of claim 30, wherein the chemically sensitive layer comprises a combination of colorimetric and luminescent reagents.

43. The device of claim 30, wherein the chemically sensitive layer comprises a combination of analyte-sensitive colorimetric reagent and analyte-insensitive luminescent reagent.

44. The device of claim 30, wherein the chemically sensitive layer comprises a oxygen-sensitive reagent.

45. The device of claim 30, wherein the chemically sensitive layer comprises a moisture-sensitive reagent.

46. The device of claim 30, wherein the chemically sensitive layer comprises a luminescent reagent selected from the group consisting of a porphyrin, a polycyclic aromatic hydrocarbon, a long-wave absorbing dye, a metal organic complex of ruthenium, a metal organic complex of osmium, a metal organic complex of iridium, a metal organic complex of gold, and a metal organic complex of platinum.

47. The device of claim 30, wherein the chemically sensitive layer comprises a solvatochromic reagent.

48. The device of claim 30, wherein the chemically sensitive layer comprises a pH reagent.

49. The device of claim 30, wherein the chemically sensitive layer comprises a thin film having a thickness in the range of about 0.5 to about 100 micrometers.

50. The device of claim 30, wherein each of the predefined number of barrier coatings comprises a thin film having a thickness in the range of about 1 nanometer to about 10 micrometers.

51. The device of claim 30, wherein the propagated wave produced by the light source has a spectral range of emission from about 150 nanometers to about 2500 nanometers.

52. A method for measuring barrier properties of coating arrays, the method comprising:
  applying a chemically sensitive layer to an exterior surface of at least one waveguide, where the chemically sensitive layer has at least one characteristic that changes in response to exposure to a material of interest;
  applying a predefined number of barrier coatings to the chemically sensitive layer, each of the predefined number of barrier coatings having a barrier property with respect to the material of interest;
  transmitting a wave through the at least one waveguide;
  exposing the at least one coated waveguide to the material of interest;
  detecting an impact associated with the propagated wave and the material of interest; and
  correlating the detected impact with a value of a barrier property for each of the array of barrier coatings.

53. The method of claim 52, where applying the barrier coatings to the chemically sensitive layer further comprises applying each of the barrier coatings about the circumference of the at least one waveguide.

54. The method of claim 53, where the at least one waveguide comprises a plurality of waveguides, and where one of the plurality of barrier coatings is deposited on a corresponding one of the plurality of waveguides.

55. The method of claim 52, where applying the barrier coatings to the chemically sensitive layer further comprises applying each of the barrier coatings about the circumference of the at least one waveguide in an abutting relationship.

56. The method of claim 55, where the at least one waveguide comprises a plurality of waveguides, and where one of the plurality of barrier coatings is deposited on a corresponding one of the plurality of waveguides.

57. The method of claim 52, where the barrier property comprises permeability.

58. The method of claim 52, where the chemically sensitive layer comprises a luminescent reagent.

59. The method of claim 52, where the chemically sensitive layer comprises a polymeric material.

60. The method of claim 52, where the predefined number of barrier coatings are selected from the group consisting of oxides, nitrides and oxinitrides of silicon, aluminum, zinc, boron and other metals, ceramics, polyvinyl alcohol, ethylene vinyl alcohol copolymers, polyvinyl dichloride, different types of nylon, acrylics, cellophane, polyethylene terephtalate, PVC, PCTFE, polypropylene, sol-gels and combinations thereof.

61. The method of claim 52, further comprising containing the at least one waveguide with the chemically sensitive layer coating and the predefined number of barrier coatings and the material of interest within a cell.

62. The method of claim 52, where the material of interest is selected from the group consisting of oxygen, water, moisture, water vapor, organic and inorganic vapors and combinations thereof.

63. The method of claim 52, where the impacts on the propagated wave are associated with a change in a chemically sensitive layer characteristic selected from the group consisting of absorption spectrum, refractive index, luminescence intensity, luminescence lifetime, luminescence spectrum and combinations thereof.

64. The method of claim 52, where detecting an impact associated with the propagated wave and the material of interest further comprises determining a difference in characteristic of a forward-propagated wave and an associated back-propagated wave.

65. A method for measuring barrier properties of coating arrays, the method comprising:
  applying a chemically sensitive layer about the circumference of an exterior surface of at least one waveguide, where the chemically sensitive layer has at least one characteristic that changes in response to exposure to a material of interest;
  applying an array of barrier coatings to the chemically sensitive layer such that the barrier coatings extend about the circumference of the at least one waveguide, each of the array of barrier coatings having a barrier property with respect to the material of interest;
  transmitting a first wave through the at least one waveguide;
  detecting a first resultant wave associated with the first wave and each of the array of barrier coatings;

exposing the at least one waveguide with the applied array of barrier coatings to the material of interest;

transmitting a second wave through the at least one waveguide;

detecting a second resultant wave associated with the second wave and each of the array of barrier coatings;

determining an impact associated with a difference between the first resultant wave and the second resultant wave for each of the array of barrier coatings; and correlating the impact with a value of a barrier property for each of the array of barrier coatings.

66. The method of claim 65, where applying the barrier coatings to the chemically sensitive layer further comprises applying each of the barrier coatings in an abutting relationship.

67. The method of claim 65, where the barrier property comprises permeability.

68. The method of claim 65, where the chemically sensitive layer comprises a luminescent reagent incorporated into a polymeric material.

69. The method of claim 65, where the chemically sensitive layer comprises a luminescent reagent incorporated into an inorganic material.

70. The method of claim 65, where the chemically sensitive layer comprises a colorimetric dye incorporated into a polymeric material.

71. The method of claim 65, where the chemically sensitive layer comprises a colorimetric dye incorporated into an inorganic material.

72. The method of claim 65, where the array of barrier coatings is selected from the group consisting of oxides, nitrides and oxinitrides of silicon, aluminum, zinc, boron and other metals, ceramics, polyvinyl alcohol, ethylene vinyl alcohol copolymers, polyvinyl dichloride, different types of nylon, acrylics, cellophane, polyethylene terephtalate, PVC, PCTFE, polypropylene, sol-gels and combinations thereof.

73. The method of claim 65, further comprising containing the at least one waveguide with the chemically sensitive layer coating and the array of barrier coatings and the material of interest within a cell.

74. The method of claim 65, where the material of interest is selected from the group consisting of oxygen, water, moisture, water vapor, organic and inorganic vapors and combinations thereof.

75. The method of claim 65, where the impact is associated with a change in a chemically sensitive layer characteristic selected from the group consisting of absorption spectrum, refractive index, luminescence intensity, luminescence lifetime, luminescence spectrum and combinations thereof.

76. The method of claim 65, where the at least one waveguide comprises a plurality of waveguides, and where one of the plurality of barrier coatings is deposited on a corresponding one of the plurality of waveguides.

* * * * *